(12) United States Patent
Darling et al.

(10) Patent No.: US 11,343,997 B2
(45) Date of Patent: May 31, 2022

(54) ALFALFA VARIETY AFX176086

(71) Applicant: AGRIGENETICS, INC., Indianapolis, IN (US)

(72) Inventors: Mark E Darling, Lansing, IA (US); Tracy Engh, Westby, WI (US); Kathleen Frost, Onalaska, WI (US); Jonathan M Reich, Woodland, CA (US); Lindsey Rushford, La Crosse, WI (US); Tim Schneider, West Salem, WI (US); Justin Valletta, Bangor, WI (US); Steven Wagner, Milton, WI (US)

(73) Assignee: AGRIGENETICS, INC.

( * ) Notice: Subject to any disclaimer, the term of this patent is extended or adjusted under 35 U.S.C. 154(b) by 0 days.

(21) Appl. No.: 17/067,269

(22) Filed: Oct. 9, 2020

(65) Prior Publication Data

US 2022/0110289 A1    Apr. 14, 2022

(51) Int. Cl.
*A01H 6/54* (2018.01)
*A01H 5/00* (2018.01)
*A01H 5/10* (2018.01)

(52) U.S. Cl.
CPC ............ *A01H 6/544* (2018.05); *A01H 5/00* (2013.01); *A01H 5/10* (2013.01)

(58) Field of Classification Search
None
See application file for complete search history.

(56) References Cited

U.S. PATENT DOCUMENTS 8,957,283 B1 * 2/2015 Hoard .................. A01H 5/10
800/295

OTHER PUBLICATIONS

Chukwu et al. Recovery of recurrent parent genome in a marker-assistend backcrossing against rice blast and blight infections using functional markers and SSRs. (2020) Plants; vol. 9; pp. 1-15 (Year: 2020).*

* cited by examiner

*Primary Examiner* — Cathy Kingdon Worley

(57) ABSTRACT

A novel alfalfa variety designated AFX176086 and seed, plants and plant parts thereof are provided. Methods for producing an alfalfa plant comprise crossing alfalfa variety AFX176086 with another alfalfa plant. Methods for producing an alfalfa plant containing in its genetic material one or more traits transgenes or locus conversions introgressed into AFX176086 through backcross conversion and/or transformation are provided and the alfalfa seed, plant and plant part produced thereby. Alfalfa seed, plants or plant parts produced by crossing alfalfa variety AFX176086 or a locus or trait conversion of AFX176086 with another alfalfa plant or population are disclosed. Alfalfa populations derived from alfalfa variety AFX176086, methods for producing other alfalfa populations derived from alfalfa variety AFX176086 and the alfalfa populations and their parts derived by the use of those methods.

20 Claims, No Drawings

ALFALFA VARIETY AFX176086

FIELD OF INVENTION

This invention is in the field of alfalfa (*Medicago sativa*) breeding, specifically relating to an alfalfa variety designated AFX176086.

BACKGROUND OF THE INVENTION

Alfalfa (*Medicago sativa* L., also known as lucerne) is one of the world's most valuable forage legumes. It is grown for hay, pasture and silage, and is valued highly as a livestock feed. Alfalfa is highly effective in nitrogen fixation and is frequently planted in crop rotation to replenish nutrients depleted from the soil by other crops such as corn.

Alfalfa originated in the Near East, in the area extending from Turkey to Iran and north into the Caucasus. From the great diversity of forms within the genus *Medicago*, two species, *M. sativa* and *M. falcate*, have become important forage plants. These species are mainly tetraploid, with 32 chromosomes, although diploid forms are known.

The commercial production of seeds for growing alfalfa plants normally involves four stages, the production of breeder, foundation, certified and registered seeds. Breeder seed is the initial increase of seed of the strain which is developed by the breeder and from which foundation seed is derived. Foundation seed is the second generation of seed increase and from which certified seed is derived. Certified seeds are used in commercial crop production and are produced from foundation or certified seed. Foundation seed normally is distributed by growers or seedsmen as planting stock for the production of certified seed.

SUMMARY OF THE INVENTION

Provided is a novel alfalfa variety, designated AFX176086 and processes for making and using AFX176086. Seed of alfalfa variety AFX176086, plants of alfalfa variety AFX176086, plant parts of alfalfa variety AFX176086, and processes for making and using an alfalfa plant are provided. The plant part may comprise at least one cell of alfalfa variety AFX176086 or modified as described herein. Methods of breeding that comprise crossing alfalfa variety AFX176086 with another alfalfa plant are described. In one aspect, processes for making an alfalfa plant containing in its genetic material one or more traits introgressed into AFX176086 through backcross conversion and/or transformation, and to the alfalfa seed, plant and plant part produced by such introgression are provided. Plant cells and plants, seeds and plant parts comprising at least one cell of alfalfa variety AFX176086 or a locus conversion of variety AFX176086 are provided. Alfalfa seeds, plants or plant parts produced by crossing the alfalfa variety AFX176086 or an introgressed trait conversion of AFX176086 with another alfalfa population or variety. Alfalfa populations derived from alfalfa variety AFX176086 and processes for making other alfalfa populations derived from alfalfa variety AFX176086 are provided as well as the alfalfa populations and their parts derived by the use of those processes.

DETAILED DESCRIPTION OF THE INVENTION

Alfalfa is a herbaceous perennial legume characterized by a deep tap root showing varying degrees of branching. Erect or semi-erect stems bear an abundance of leaves. The number of stems arising from a single woody crown may vary from just a few to fifty or more. New stems develop when older ones mature or have been cut or grazed. Flowers are borne on axillary racemes which vary greatly in size and number of flowers. Flower color is predominantly purple, or bluish-purple, but other colors occur. The fruit is a legume, or pod, usually spirally coiled in *M. sativa*. Seeds are small and the color varies from yellow to brown. Alfalfa is widely adapted to temperature and soil conditions, except for humid tropical conditions. Reproduction in alfalfa is mainly by cross-fertilization, but substantial self-pollination may also occur. Cross-pollination is effected largely by bees.

The following terms are used in this application:

Acid-Detergent Fiber ("ADF") approximates the amount of cellulose fiber and ash present in a feed. Forages with high ADF values are less digestible than forages with low ADF values and, therefore, provide fewer nutrients to the animal through digestion. Because of this relationship, ADF serves as an estimate of digestibility and can be used by nutritionists to predict the energy that will be available from a forage.

AOSCA. Abbreviation for Association of Official Seed Certifying Agencies.

Crude Protein ("CP") is determined by measuring the total nitrogen concentration of a forage and multiplying it by 6.25. This technique measures not only the nitrogen present in true proteins, but also that present in non-protein forms such as ammonia, urea and nitrate. Because most of the non-protein forms of nitrogen are converted to true protein by the rumen microorganisms, CP is considered by nutritionists to provide an accurate measure of the protein that will be available to ruminant animals from a given forage.

DM. Abbreviation for Dietary Dry Matter. Used to calculate yield.

Fall Dormancy (Dormancy or "FD") Most alfalfa plants go dormant in the fall in preparation for winter. The onset of dormancy is triggered by a combination of day length and temperature and is genotype dependent. Fall dormancy scores indicate the dormancy response of alfalfa genotypes by quantifying the height of alfalfa measured in October relative to a set of standard check varieties. The standard fall dormancy test requires that plants are cut off in early September with plant height measured in early-mid October. Early fall dormant types show very little growth after the September clipping, later fall dormant type demonstrate substantial growth.

Alfalfa is classified into fall dormancy groups, numbered 1 to 11, where Dormancy Group 1 is most dormant and suited for cold climates (such varieties would stop growing and go dormant over winter), and Dormancy Group 7-11 are very non-dormant and suited for very hot climates (such varieties would have high growth rates over a very long growing season and would have relatively high winter activity). The NA&MLVRB recognizes standard or check varieties for Dormancy Groups 1-11, Check cultivars are listed in the NAAIC Standard Tests to Characterize Alfalfa Cultivars, maintained online on the NAAIC's website. The check varieties for the various fall dormancy ratings/Dormancy Groups (corresponding to the rating scale used by the Certified Alfalfa Seed Council (CASC)) are as follows:

Check Cultivars: A single set of check cultivars representing fall dormancy classes (FDC) 1 to 11 are designated. These check cultivars have been selected to maintain the intended relationship between the original set of nine check cultivars (Standard Tests, March 1991, updated in 1998) and to have minimal variation across environments. The actual fall dormancy rating (FDR) based on the average University of California regression and the Certified Alfalfa Seed Council Class that each check cultivar represents are listed below.

| Variety | FDR | FDC |
|---|---|---|
| Maverick | 0.8 | 1.0 |
| Vernal | 2.0 | 2.0 |
| 5246 | 3.4 | 3.0 |
| Legend | 3.8 | 4.0 |
| Archer | 5.3 | 5.0 |
| ABI 700 | 6.3 | 6.0 |
| Dona Ana | 6.7 | 7.0 |
| Pierce | 7.8 | 8.0 |
| CUF 101 | 8.9 | 9.0 |
| UC-1887 | 9.9 | 10.0 |
| UC-1465 | 11.2 | 11.0 |

Fall dormancy regression (FDR) number corresponds to the fall dormancy value calculated using the University of California regression equation.

Fall dormancy class (FDC) number corresponds to the fall dormancy class used by the Certified Alfalfa Seed Council (CASC)

In Vitro True Digestibility ("IVTD") is a measurement of digestibility utilizing actual rumen microorganisms. Although ADF serves as a good estimate of digestibility, IVID provides a more accurate assessment of a forage's feeding value by actually measuring the portion of a forage that is digested. This process is more expensive and time consuming than the analysis for ADF concentrations of a feed, but provides a more meaningful measure of forage digestibility. Techniques for measuring in vitro digestibility are based on incubating a forage sample in a solution containing rumen microorganisms for an extended period of time (usually 48 hours).

Milk Per Ton is an estimate of the milk production that could be supported by a given forage when fed as part of a total mixed ration. The equation for calculating milk per ton uses NDF and ADF to calculate total energy intake possible from the forage. After subtracting the amount of energy required for daily maintenance of the cow, the quantity of milk that could be produced from the remaining energy is calculated. The ratio of milk produced to forage consumed is then reported in the units of pounds of milk produced per ton of forage consumed. Milk per ton is useful because it characterizes forage quality in two terms that a dairy farmer is familiar with: pounds of milk and tons of forage. By combining milk per ton and dry matter yield per acre, we arrive at "milk per acre". This term is widely used to estimate the economic value of a forage.

NAAIC. North America Alfalfa Improvement Conference, which is the governing body over the NA&MLVRB NA&MLVRB. National Alfalfa and Miscellaneous Legume Variety Review Board. The NA&MLVRB is administered by the Association of Official Seed Certifying Agencies (AOSCA).

NAVRB. Abbreviation for National Alfalfa Variety Review Board. NAVRB recently changed its name to "National Alfalfa and Miscellaneous Legume Variety Review Board" (NA&MLVRB).

Neutral-Detergent Fiber ("NDF") represents the total amount of fiber present in the alfalfa. Because fiber is the portion of the plant most slowly digested in the rumen, it is this fraction that fills the rumen and becomes a limit to the amount of feed an animal can consume. The higher the NDF concentration of a forage, the slower the rumen will empty reducing what an animal will be able to consume. For this reason, NDF is used by nutritionists as an estimate of the quantity of forage that an animal will be able to consume. Forages with high NDF levels can limit intake to the point that an animal is unable to consume enough feed to meet their energy and protein requirements.

Potato leafhopper (PLH) resistant variety. Potato Leafhopper Resistance is a reaction of the alfalfa host plant which enables it to avoid serious damage from potato leafhopper feeding. The resistant plant reaction is to demonstrate normal growth in the presence of high populations of potato leafhoppers, whereas susceptible plants show significant stunting and yellowing in reaction to insect feeding. The convention used for measuring PLH damage disclosed herein is patterned after standard tests used for measuring damage/resistance to other pests. Individual plants are scored on a (1-5) scale, where 1=no damage evident and 5=severe stunting and yellowing. Plants scored as 1 and 2 are classified as resistant. The average severity index (ASI) of a variety is the average damage score for 100 random plants. The ASI is often used in combination with percent resistance to characterize pest resistance of alfalfa cultivars. Using this standard convention, an alfalfa variety described as being resistant to PLH has between (31%-50%) of the plants in the variety being scored 1 or 2 in a standard test to measure PLH reaction. Individual alfalfa plants or clones (clonal propagules of individual genotypes) with a resistance score of 1 have very high resistance; a score of 3 show moderate resistance; and a score of 5 show no resistance.

Relative Feed Value ("RFV") is a numeric value assigned to forages based upon their ADF and NDF values. In this calculation, NDF is used to estimate the dry matter intake expected for a given forage, and the ADF concentration is used to estimate the digestibility of the forage. By combining these two relationships, an estimate of digestible dry matter intake is generated. This value is then reported relative to a standard forage (fall bloom alfalfa=100) and can be used to rank forages based on their anticipated feeding value. Relative feed value has been accepted in many areas as a means of estimating forage feeding value and is commonly used in determining the price of alfalfa at tested hay auctions.

Relative Forage Quality ("RFQ") is a numeric value that estimates the energy content of forage for total digestible nutrients as recommended by the National Research Council. Values are assigned to forages based upon the actual fiber digestibility (NDFd) and Total Digestible Nutrients (TDN). By combining these two relationships, an estimate of how the forage will perform in animal rations is predicted. Relative forage quality has been accepted in many areas as a means of estimating forage feeding value and is commonly used in determining the price of alfalfa at tested hay auctions or for on farm use.

Synthetic variety ("SYN") is developed by intercrossing a number of genotypes with specific favorable characteristics and/or overall general favorable qualities. Synthetic (SYN) variety can be developed by using clones, inbreds, open pollinated varieties, and/or individual heterozygous plants.

TA. Tons per Acre. Used to calculate yield.

Total Digestible Nutrients ("TDN") is an estimate of the energy content of a feedstuff based on its relative proportions of fiber, fat, carbohydrate, crude protein, and ash. Because it is expensive to measure each of these components, TDN is usually estimated from ADF or IVTD. Although still used in some areas as a criteria for evaluating alfalfa hay at auctions, TDN has been shown to overestimate the energy content of low quality forages and thus does not accurately reflect the nutritional value of all forage samples.

Winterhardiness ("WH") is a measure of the ability of an alfalfa plant to survive the stresses associated with winter. Cold hardiness is a key feature of the winterhardiness trait. There is a general relationship between fall dormancy and winterhardiness, the early fall dormant types (FD2-5) being more winterhardy than the later fall dormant types (FD6-9). The winterhardiness rating used in this patent are derived from the standard test for measuring winter survival. The standard test measures plant survival and spring vigor following a winter stress enough to substantially injure check varieties.

Alfalfa varieties are heterogeneous populations formed by intercrossing a number of alfalfa clones. Pest resistance in alfalfa varieties is commonly measured in standard tests as the percent of plants in the population that express the resistance trait. The National Alfalfa Variety Review Board in accordance with the recommendation of the North American Alfalfa Improvement Conference has adopted a convention that uses percent resistant plants to describe levels of pest resistance. This convention is as follows: (0-5%)=susceptible, (6-15%)=low resistance, (16-30%)=moderate resistance, (31-50%)=resistance, and (>51%)=high resistance. With most pests, economic losses due to pest damage are minimized or eliminated with varieties containing resistance to high resistance. Individual plants can also have varying levels of resistance.

Alfalfa is an auto-tetraploid and is frequently self-incompatible in breeding. When selfed, little or no seed is produced, or the seed may not germinate, or when it does, may have reduced vigor and may later stop growing. Typically, fewer than five percent of selfed crosses produce seed. When a very small population is crossbred, inbreeding depression occurs, and traits of interest, such as quality, yield, and resistance to a large number of pests (e.g., seven or eight different pests), are lost. Thus, producing a true breeding parent for hybrids is not possible, which complicates breeding substantially.

Efforts to develop alfalfa varieties having improved traits and increased production have focused on breeding for disease, insect, or nematode resistance, persistence, adaptation to specific environments, increased yield, and improved quality. Breeders have had some success in breeding for increased herbage quality and forage yield, although there are significant challenges.

Breeding programs typically emphasize maximizing heterogeneity of a given alfalfa variety to improve yield and stability. However, this generally results in wide variations in characteristics such as flowering dates, flowering frequency, development rate, growth rate, fall dormancy and winter hardiness. Prior art breeding methods do not emphasize improving the uniformity of these characteristics.

Some sources indicate that there are nine major germplasm sources of alfalfa: M. falcata, ladak, M. varia, Turkistan, Flemish, Chilean, Peruvian, Indian, and African. Tissue culture of explant source tissue, such as mature cotyledons and hypocotyls, demonstrates the regeneration frequency of genotypes in most cultivars is only about 10 percent. Seitz-Kris, M. H. and E. T. Bingham, In vitro Cellular and Developmental Biology 24 (10):1047-1052 (1988). Efforts have been underway to improve regeneration of alfalfa plants from callus tissue. E. T. Bingham, et. al., Crop Science 15:719-721 (1975).

Disclosed herein are methods for producing first-generation synthetic variety alfalfa seed comprising crossing a first parent alfalfa plant with a second parent alfalfa plant and harvesting resultant first-generation (F1) alfalfa seed, wherein said first or second parent alfalfa plant is one of the alfalfa plants of the present invention described above.

Alfalfa having agronomically desirable traits and breeding methods that result in a high degree of hybridity, uniformity of selected traits, and acceptable seed yields are described herein.

Methods of obtaining alfalfa populations using cytoplasmic male sterile alfalfa populations (A populations), maintainer alfalfa populations (B populations), and male fertile pollenizer populations (C populations) are provided.

Male sterile A populations may be identified by evaluating pollen production using the Pollen Production Index (P.P.I.), which recognizes four distinct classes: 1. Male Sterile Plants (MS) PPI=0 for which no visible pollen can be observed with the naked eye when flower is tripped with a black knife blade; 2. Partial Male Sterile Plant (PMS) PPI=0.1 for which a trace of pollen is found with the naked eye when flower is tripped with a black knife blade; 3. Partial Fertile Plant (PF) PPI=0.6 for which less than a normal amount of pollen can be observed with the naked eye when flower is tripped with a black knife blade; and 4. Fertile Plant (F) PPI=1.0 for which normal amounts of pollen can be observed when flower is tripped with a black knife blade.

The cells of the cytoplasmic male sterile (A population) alfalfa plants contain sterile cytoplasm and the non-restorer gene. The maintainer population (B population) is a male and female fertile plant, and when crossed with an A population plant, maintains the male sterility of the cytoplasmic male sterile plant in the progeny. The cells of a maintainer population plant contain normal cytoplasm and the non-restorer gene. Methods for identifying cytoplasmic male sterile and maintainer populations of alfalfa are well known to those versed in the art of alfalfa plant breeding (e.g., see U.S. Pat. No. 3,570,181, which is incorporated by reference herein). A pollenizer population (C population) is a fertile plant containing both male and female parts.

Cytoplasmic male sterile populations may be maintained by vegetative cuttings. Maintainer populations can be maintained by cuttings or self-pollination. Male sterile plants can be obtained by cross-pollinating cytoplasmic male sterile plants with maintainer plants. Pollenizer populations can be maintained by selfing or, if more than two clones are used, by cross-pollination.

At least one of the alfalfa plant populations used in developing alfalfa plants according to the methods described herein may have at least one desirable agronomic trait, which may include, for example, resistance to disease or insects, cold tolerance, increased persistence, greater forage yield or seed yield, improved forage quality, uniformity of growth rate, and uniformity of time of maturity.

In the controlled pollination step, the cytoplasmic male sterile plants are typically grown in separate rows from the maintainer plants. The plants are pollinated by pollen-carrying insects, such as bees. Segregating the male sterile and maintainer plants facilitates selective harvest of seed from the cytoplasmic male sterile plants. The male sterile seed and male fertile seed can be provided as a random mixture of the seed in a ratio of about 4:1, which would provide for random distribution of the male sterile and male fertile plants grown therefrom and random pollination of the alfalfa plants. As one of skill in the art will appreciate, one could also practice the method of the invention using designed distribution of male sterile and male fertile populations within a field and subsequent pollination by pollen-carrying insects.

One of ordinary skill in the art will appreciate that any suitable male sterile population, maintainer population, and pollenizer population could be successfully employed in the practice of the method of the invention.

In an embodiment, a tissue culture of regenerable cells derived, in whole or in part, from an alfalfa plant of synthetic variety named AFX176086 is provided. In one embodiment, cells may be regenerated into plants having substantially all the morphological and physiological characteristics of the synthetic alfalfa variety named AFX176086 that are described in the attached tables. Some embodiments include a tissue culture that includes cultured cells derived, in whole or in part, from a plant part selected from the group consisting of leaves, roots, root tips, root hairs, anthers, pistils, stamens, pollen, ovules, flowers, seeds, embryos, stems, buds, cotyledons, hypocotyls, cells and protoplasts. Another embodiment is an alfalfa plant regenerated from such a tissue culture, having all the morphological and physiological characteristics of synthetic alfalfa variety AFX176086.

Tissue culture of alfalfa is further described in Saunders, J. W. and Bingham, E. T., (1971) Production of alfalfa plants from callus tissue, Crop Sci 12; 804-808, and incorporated herein by reference. Methods for regeneration of alfalfa plants from tissue culture are described in U.S. Pat. No. 5,324,646 issued Jun. 28, 1994, which is hereby incorporated by reference. Additionally, methods for improving heritable somatic embryogenesis in alfalfa, which may be controlled by relatively few genes, are provided, for example, methods of isolation of the genetic control of embryogenesis and breeding methods which would incorporate such information.

A plant may include plant cells, plant protoplasts, plant cells of tissue culture from which alfalfa plants can be regenerated, plant calli, plant clumps, and plant cells that are intact in plants or parts of plants such as pollen, flowers, seeds, leaves, roots, stems, and the like.

The advent of new molecular biological techniques has allowed the isolation and characterization of genetic elements with specific functions, such as encoding specific protein products. DNA sequences, whether from a different species or from the same species, which are inserted into the genome using transformation are referred to herein collectively as "transgenes". Provided are methods of modifying alfalfa variety AFX176086 by genome editing and locus conversions of alfalfa variety AFX176086 produced by editing the genome of alfalfa variety AFX176086. In some embodiments of the invention, a transformed or edited variant of AFX176086 may contain at least one transgene and/or gene edit but could contain at least 1, 2, 3, 4, 5, 6, 7, 8, 9, 10 and/or no more than 15, 14, 13, 12, 11, 10, 9, 8, 7, 6, 5, 4, 3, or 2 transgenes and/or gene edits. Methods for producing transgenic and edited plants and their used to create transformed and edited versions of alfalfa variety AFX176086 are provided.

Provided are plants, seeds and plant parts of alfalfa variety AFX176086 further comprising a locus conversion, and method for making and using such plants, seeds and plant parts. A locus conversion, also called a trait conversion, can be a native trait, an edited trait, or a transgenic trait. In addition, a recombination site itself, such as an FRT site, Lox site or other site specific integration site, may be inserted by backcrossing and utilized for direct insertion of one or more genes of interest into a specific plant variety. The trait of interest is transferred from the donor parent to the recurrent parent.

A single locus may contain several transgenes or edits, such as a transgene for disease resistance that, in the same expression vector, also contains a transgene for herbicide tolerance or resistance. The gene for herbicide tolerance or resistance may be used as a selectable marker and/or as a phenotypic trait. A single locus conversion of a site specific integration system allows for the integration of multiple genes at a known recombination site in the genome. At least one, at least two or at least three and less than ten, less than nine, less than eight, less than seven, less than six, less than five or less than four locus conversions may be introduced into the plant by backcrossing, introgression or transformation to express the desired trait, while the plant, or a plant grown from the seed, plant part or plant cell, otherwise retains the phenotypic characteristics of the deposited seed when grown under the same environmental conditions.

The modified variety AFX176086 or variety AFX176086 further comprising a locus conversion may be further characterized as having all of, the same or essentially all of or essentially the same phenotypic characteristics or physiological and morphological characteristics of alfalfa variety AFX176086, for example, as are listed in one or more of the tables herein, when grown under the same or similar environmental conditions and/or may be characterized by percent identity to AFX176086 as determined by molecular markers, such as SSR markers or SNP markers. Examples of percent identity determined using markers include at least 95%, 96%, 97%, 98%, 99% or 99.5%. Traits can be used by those of ordinary skill in the art to characterize the plants disclosed herein. Traits are commonly evaluated at a significance level, such as a 1%, 5% or 10% significance level, when measured in plants grown in the same environmental conditions.

The backcross or locus conversion may result from either the transfer of a dominant allele or a recessive allele. Selection of progeny containing the trait of interest can be accomplished by direct selection for a trait associated with a dominant allele. Transgenes transferred via backcrossing typically function as a dominant single gene trait and are relatively easy to classify. Selection of progeny for a trait that is transferred via a recessive allele, such as the waxy starch characteristic, requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Numerous methods for plant transformation have been developed, including biological and physical plant transformation protocols. Specific to alfalfa, see, for example, "Efficient *Agrobacterium*-mediated transformation of alfalfa using secondary somatic embryogenic callus", Journal of the Korean Society of Grassland Science 20 (1): 13-18 2000, E. Charles Brummer, "Applying Genomics to Alfalfa Breeding Programs" Crop Sci. 44:1904-1907 (2004), and "Genetic transformation of commercial breeding populations of alfalfa (*Medicago sativa*)" Plant Cell Tissue and Organ Culture 42 (2): 129-140 1995 which are incorporated by reference for this purpose. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

The most prevalent types of plant transformation involve the construction of an expression vector. Such a vector comprises a DNA sequence that contains a gene under the control of or operatively linked to a regulatory element, for example a promoter. The vector may contain one or more genes and one or more regulatory elements.

A genetic trait which has been engineered into the genome of a particular alfalfa plant using transformation techniques or gene editing, could be moved into the genome of another population using traditional breeding techniques that are well known in the plant breeding arts. For example, a backcrossing approach may be used to move a transgene from a transformed or edited alfalfa plant to an elite population, and the resulting progeny would then comprise the transgene(s) or edited genes.

Various genetic elements can be introduced into the plant genome using transformation. These elements include, but are not limited to, genes; coding sequences; inducible, constitutive, and tissue specific promoters; enhancing sequences; and signal and targeting sequences. For example, see the traits, genes and transformation methods listed in U.S. Pat. No. 6,118,055.

Transgenic plants which produce a foreign protein in commercial quantities are provided. For example, techniques for the selection and propagation of transformed plants, including those well understood in the art, may yield a plurality of transgenic plants that can be harvested, such as in a conventional manner, and a foreign protein then can be extracted from a tissue of interest or from total biomass. Methods for protein extraction from plant biomass are provided, such as those accomplished by methods which are discussed, for example, by Heney and Orr, Anal. Biochem. 114: 92-6 (1981).

A genetic map can be generated, primarily via conventional Restriction Fragment Length Polymorphisms (RFLP), Polymerase Chain Reaction (PCR) analysis, Simple Sequence Repeats (SSR) and Single Nucleotide Polymorphisms (SNP) that identifies the approximate chromosomal location of the integrated DNA molecule. For exemplary methodologies in this regard, see Glick and Thompson, Methods in Plant Molecular Biology and Biotechnology 269-284 (CRC Press, Boca Raton, 1993). Specific to alfalfa, see Construction of an improved linkage map of diploid alfalfa (*Medicago sativa*), Theoretical and Applied Genetics 100 (5): 641-657 March, 2000 and Isolation of a full-length mitotic cyclin cDNA clone CycIIIMs from *Medicago sativa*: Chromosomal mapping and expression, Plant Molecular Biology 27 (6): 1059-1070 1995 which are incorporated by reference for this purpose.

Wang et al. discuss "Large Scale Identification, Mapping and Genotyping of Single-Nucleotide Polymorphisms in the Human Genome", Science, 280:1077-1082, 1998, and similar capabilities are becoming increasingly available for many plant genomes. Map information concerning chromosomal location is useful for proprietary protection of a subject transgenic plant. If unauthorized propagation is undertaken and crosses made with other germ plasm, the map of the integration region can be compared to similar maps for suspect plants to determine if the latter have a common parentage with the subject plant. Map comparisons would involve hybridizations, RFLP, PCR, SSR and sequencing, all of which are conventional techniques. SNPs may also be used alone or in combination with other techniques.

Provided are plants genetically engineered to express various phenotypes of agronomic interest and methods for making and using such plants. Through the transformation of alfalfa gene expression can be altered to enhance, for example, disease resistance, insect resistance, herbicide resistance, agronomic properties, grain quality, nutritional quality, digestibility and other traits.

Transgenes and transformation methods facilitate engineering of the genome of plants to contain and express heterologous genetic elements, such as foreign genetic elements, or additional copies of endogenous elements, or modified versions of native or endogenous genetic elements in order to alter at least one trait of a plant in a specific manner. Any sequences, such as DNA, whether from a different species or from the same species, which have been stably inserted into a genome using transformation are referred to herein collectively as "transgenes" and/or "transgenic events". Transgenes can be moved from one genome to another using breeding techniques which may include, for example, crossing, backcrossing or double haploid production. In some embodiments, a transformed variant of AFX176086 may comprise at least one transgene but could contain at least 1, 2, 3, 4, 5, 6, 7, 8, 9, 10 and/or no more than 15, 14, 13, 12, 11, 10, 9, 8, 7, 6, 5, 4, 3, or 2. Transformed versions of alfalfa variety AFX176086 containing and inheriting the transgene thereof are provided.

Numerous methods for plant transformation have been developed, including biological and physical plant transformation protocols. In addition, expression vectors and in vitro culture methods for plant cell or tissue transformation and regeneration of plants are available.

In general, methods to transform, modify, edit or alter plant endogenous genomic DNA include altering the plant native DNA sequence or a pre-existing transgenic sequence including regulatory elements, coding and non-coding sequences. These methods can be used, for example, to target nucleic acids to pre-engineered target recognition sequences in the genome. Such pre-engineered target sequences may be introduced by genome editing or modification. As an example, a genetically modified plant variety is generated using "custom" or engineered endonucleases such as meganucleases produced to modify plant genomes (see e.g., WO 2009/114321; Gao et al. (2010) Plant Journal 1:176-187). Another site-directed engineering method is through the use of zinc finger domain recognition coupled with the restriction properties of restriction enzyme. See e.g., Urnov, et al., (2010) Nat Rev Genet. 11(9):636-46; Shukla, et al., (2009) Nature 459 (7245):437-41. A transcription activator-like (TAL) effector-DNA modifying enzyme (TALE or TALEN) is also used to engineer changes in plant genome. See e.g., US20110145940, Cermak et al., (2011) Nucleic Acids Res. 39(12) and Boch et al., (2009), Science 326(5959): 1509-12. Site-specific modification of plant genomes can also be performed using the bacterial type II CRISPR (clustered regularly interspaced short palindromic repeats)/Cas (CRISPR-associated) system. See e.g., Belhaj et al., (2013), Plant Methods 9: 39; The Cas9/guide RNA-based system allows targeted cleavage of genomic DNA guided by a customizable small noncoding RNA in plants (see e.g., WO 2015026883A1).

Plant transformation methods may involve the construction of an expression vector. Such a vector comprises a DNA sequence that contains a gene under the control of or operatively linked to a regulatory element, for example a promoter. The vector may contain one or more genes and one or more regulatory elements.

A transgenic event which has been stably engineered into the germ cell line of a particular alfalfa plant using transformation techniques, could be moved into the germ cell line of another variety using traditional breeding techniques that are well known in the plant breeding arts. These varieties can then be crossed to generate an alfalfa plant such as alfalfa variety plant AFX176086 which comprises a transgenic event. For example, a backcrossing approach is commonly used to move a transgenic event from a transformed alfalfa plant to another variety, and the resulting progeny would then comprise the transgenic event(s). Also, if an inbred variety was used for the transformation then the transgenic plants could be crossed to a different inbred in order to produce a transgenic alfalfa plant.

Various genetic elements can be introduced into the plant genome using transformation. These elements include, but are not limited to, genes; coding sequences; inducible, constitutive, and tissue specific promoters; enhancing sequences; and signal and targeting sequences. For example, see the traits, genes and transformation methods listed in U.S. Pat. Nos. 6,118,055 and 6,284,953. In addition, transformability of a variety can be increased by introgressing the trait of high transformability from another variety known to have high transformability, such as Hi-II. See U.S. Patent Application Publication US 2004/0016030.

With transgenic or genetically modified plants, a foreign protein can be produced in commercial quantities. Thus, techniques for the selection and propagation of transformed plants, which are well understood in the art, yield a plurality of transgenic or genetically modified plants that are harvested in a conventional manner, and a foreign protein then can be extracted from a tissue of interest or from total biomass. Protein extraction from plant biomass can be accomplished by known methods which are discussed, for example, by Sack, M. et al., *Curr. Opin. Biotech* 32: 163-170 (2015).

Transgenic events can be mapped by one of ordinary skill in the art and such techniques are well known to those of ordinary skill in the art.

Plants can be genetically engineered or modified to express various phenotypes of agronomic interest. Through the transformation or modification of alfalfa the expression of genes can be altered to enhance disease resistance, insect resistance, herbicide tolerance, agronomic traits, grain quality and other traits. Transformation can also be used to insert DNA sequences which control or help control male-sterility. DNA sequences native to alfalfa as well as non-native DNA sequences can be transformed into alfalfa and used to alter levels of native or non-native proteins. Various promoters, targeting sequences, enhancing sequences, and other DNA sequences can be inserted into the alfalfa genome for the purpose of altering the expression of proteins. Reduction of the activity of specific genes (also known as gene silencing, or gene suppression) is desirable for several aspects of genetic engineering in plants.

Many techniques for gene silencing are well known to one of skill in the art, including but not limited to knock-outs (such as by insertion of a transposable element such as mu or other genetic elements such as a FRT, Lox or other site specific integration site, antisense technology (see, e.g., U.S. Pat. Nos. 5,107,065; 5,453,566; and 5,759,829); co-suppression (e.g., U.S. Pat. No. 5,034,323), virus-induced gene silencing; target-RNA-specific ribozymes; hairpin structures (WO 99/53050 and WO 98/53083); MicroRNA; ribozymes; oligonucleotide mediated targeted modification (e.g., WO 03/076574 and WO 99/25853); Zn-finger targeted molecules (e.g., WO 01/52620; WO 03/048345; and WO 00/42219); and other methods or combinations of the above methods known to those of skill in the art.

Exemplary nucleotide sequences that may be altered by genetic engineering include, but are not limited to, those categorized below. Exemplary nucleotide sequences that may be altered by genetic engineering include, but are not limited to, those categorized below.

1. Transgenes That Confer Resistance to Insects or Disease and That Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. A plant resistant to a disease is one that is more resistant to a pathogen as compared to the wild type plant.

(B) A *Bacillus thuringiensis* protein, a derivative thereof or a synthetic polypeptide modeled thereon. DNA molecules encoding delta-endotoxin genes can be purchased from American Type Culture Collection (Manassas, Va.), for example, under ATCC Accession Nos. 40098, 67136, 31995 and 31998. Other non-limiting examples of *Bacillus thuringiensis* transgenes being genetically engineered are given in the following patents and patent applications: U.S. Pat. Nos. 5,188,960; 5,689,052; 5,880,275; 5,986,177; 7,105,332; 7,208,474; WO 91/14778; WO 99/31248; WO 01/12731; WO 99/24581; WO 97/40162 and U.S. application Ser. Nos. 10/032,717; 10/414,637; 11/018,615; 11/404,297; 11/404,638; 11/471,878; 11/780,501; 11/780,511; 11/780,503; 11/953,648; and Ser. No. 11/957,893.

(C) An insect-specific hormone or pheromone such as an ecdysteroid and juvenile hormone, a variant thereof, a mimetic based thereon, or an antagonist or agonist thereof.

(D) An insect-specific peptide which, upon expression, disrupts the physiology of the affected pest. For example, an insect diuretic hormone receptor or an allostatin. See also U.S. Pat. No. 5,266,317 disclosing genes encoding insect-specific toxins.

(E) An enzyme responsible for a hyperaccumulation of a monoterpene, a sesquiterpene, a steroid, hydroxamic acid, a phenylpropanoid derivative or another non-protein molecule with insecticidal activity.

(F) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also U.S. Pat. Nos. 6,563,020; 7,145,060 and 7,087,810.

(G) A molecule that stimulates signal transduction. For example, calmodulin cDNA clones.

(H) A hydrophobic moment peptide. See PCT application WO 95/16776 and U.S. Pat. No. 5,580,852 disclosure of peptide derivatives of Tachyplesin which inhibit fungal plant pathogens) and PCT application WO 95/18855 and U.S. Pat. No. 5,607,914 (teaches synthetic antimicrobial peptides that confer disease resistance).

(I) A membrane permease, a channel former or a channel blocker.

(J) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. Coat protein-mediated resistance may been conferred upon transformed plants against, for example, alfalfa mosaic virus, cucumber mosaic virus, tobacco streak virus, potato virus X, potato virus Y, tobacco etch virus, tobacco rattle virus and tobacco mosaic virus.

(K) An insect-specific antibody or an immunotoxin derived therefrom. For example, an antibody targeted to a critical metabolic function in the insect gut would inactivate an affected enzyme, killing the insect.

(L) A virus-specific antibody. Plants expressing recombinant antibody genes may be protected from virus attack.

(M) A developmental-arrestive protein produced in nature by a pathogen or a parasite. For example, fungal endo alpha-1,4-D-polygalacturonases facilitate fungal colonization and plant nutrient release by solubilizing plant cell wall homo-alpha-1,4-D-galacturonase.

(N) A developmental-arrestive protein produced in nature by a plant. For example, plants expressing the barley ribosome-inactivating gene may have an increased resistance to fungal disease.

(O) Genes involved in the Systemic Acquired Resistance (SAR) Response and/or the pathogenesis related genes (P) Antifungal genes. See, e.g., U.S. application Ser. Nos. 09/950,933; 11/619,645; 11/657,710; 11/748,994; 11/774,121 and U.S. Pat. Nos. 6,891,085 and 7,306,946.

(Q) Detoxification genes, such as for fumonisin, beauvericin, moniliformin and zearalenone and their structurally related derivatives. For example, see U.S. Pat. Nos. 5,716,820; 5,792,931; 5,798,255; 5,846,812; 6,083,736; 6,538,177; 6,388,171 and 6,812,380.

(R) Cystatin and cysteine proteinase inhibitors. See U.S. Pat. No. 7,205,453.

(S) Defensin genes. See, e.g., WO03000863 and U.S. Pat. Nos. 6,911,577; 6,855,865; 6,777,592 and 7,238,781.

(T) Genes conferring resistance to nematodes. See, e.g., PCT Application WO96/30517; PCT Application WO93/19181, WO 03/033651 and U.S. Pat. Nos. 6,284,948 and 7,301,069.

(U) Genes that confer resistance to *Phytophthora* Root Rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes.

(V) Genes that confer resistance to Brown Stem Rot, such as described in U.S. Pat. No. 5,689,035.

(W) Genes that confer resistance to *Colletotrichum*, such as described in US Patent publication US20090035765. This includes the Rcg locus that may be utilized as a single locus conversion.

2. Transgenes That Confer Tolerance to A Herbicide, For Example:

(A) A herbicide that inhibits the growing point or meristem, such as an imidazolinone or a sulfonylurea. Exemplary genes in this category code for mutant acetolactate synthase (ALS) and acetohydroxyacid synthase (AHAS) enzyme as described, for example, in U.S. Pat. Nos. 5,605,011; 5,013,659; 5,141,870; 5,767,361; 5,731,180; 5,304,732; 4,761,373; 5,331,107; 5,928,937; and 5,378,824; US Patent Publication No. 20070214515, and international publication WO 96/33270.

(B) Glyphosate (tolerance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cyclohexones (ACCase inhibitor-encoding genes). See, for example, U.S. Pat. No. 4,940,835, which discloses the nucleotide sequence of a form of EPSPS which can confer glyphosate tolerance. U.S. Pat. No. 5,627,061 also describes genes encoding EPSPS enzymes. See also U.S. Pat. Nos. 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491,288; and international publications EP1173580; WO 01/66704; EP1173581 and EP1173582.

Glyphosate tolerance is also imparted to plants that express a gene that encodes a glyphosate oxido-reductase enzyme as described more fully in U.S. Pat. Nos. 5,776,760 and 5,463,175. In addition, glyphosate tolerance can be imparted to plants by the over expression of genes encoding glyphosate N-acetyltransferase. See, for example, US2004/0082770; US2005/0246798; and US2008/0234130. A DNA molecule encoding a mutant aroA gene can be obtained under ATCC accession No. 39256, and the nucleotide sequence of the mutant gene is disclosed in U.S. Pat. No. 4,769,061. European Patent Application No. 0 333 033 and U.S. Pat. No. 4,975,374 disclose nucleotide sequences of glutamine synthetase genes which confer tolerance to herbicides such as L-phosphinothricin. The nucleotide sequence of a phosphinothricin-acetyl-transferase gene is provided in European Patent Nos. 0 242 246 and 0 242 236. See also, U.S. Pat. Nos. 5,969,213; 5,489,520; 5,550,318; 5,874,265; 5,919,675; 5,561,236; 5,648,477; 5,646,024; 6,177,616 B1; and 5,879,903. Exemplary genes conferring resistance to phenoxy propionic acids, cyclohexanediones and cyclohexones, such as sethoxydim and haloxyfop, are the Acc1-S1, Acc1-S2 and Acc1-S3 genes.

(C) A herbicide that inhibits photosynthesis, such as a triazine (psbA and gs+ genes), glutathione S-transferase and a benzonitrile (nitrilase gene) such as bromoxynil. Nucleotide sequences for nitrilase genes are disclosed in U.S. Pat. No. 4,810,648 to Stalker, and DNA molecules containing these genes are available under ATCC Accession Nos. 53435, 67441 and 67442.

(D) Other genes that confer tolerance to herbicides include: a gene encoding a chimeric protein of rat cytochrome P4507A1 and yeast NADPH-cytochrome P450 oxidoreductase, genes for glutathione reductase and superoxide dismutase, and genes for various phosphotransferases.

(E) A herbicide that inhibits protoporphyrinogen oxidase (protox or PPO) is necessary for the production of chlorophyll, which is necessary for all plant survival. The protox enzyme serves as the target for a variety of herbicidal compounds. PPO-inhibitor herbicides can inhibit growth of all the different species of plants present, causing their total destruction. The development of plants containing altered protox activity which are tolerant to these herbicides are described, for example, in U.S. Pat. Nos. 6,288,306 B1; 6,282,837 B1; and 5,767,373; and international patent publication WO 01/12825.

(F) Dicamba (3,6-dichloro-2-methoxybenzoic acid) is an organochloride derivative of benzoic acid which functions by increasing plant growth rate such that the plant dies.

3. Transgenes That Confer or Contribute to an Altered Grain Characteristic, Such as:

(A) Altered fatty acids, for example, by (1) Down-regulation of stearoyl-ACP desaturase to increase stearic acid content of the plant. See, e.g., WO99/64579, (2) Elevating oleic acid via FAD-2 gene modification and/or decreasing linolenic acid via FAD-3 gene modification (se, e.g., U.S. Pat. Nos. 6,063,947; 6,323,392; 6,372,965 and WO 93/11245), (3) Altering conjugated linolenic or linoleic acid content, such as in WO 01/12800, (4) Altering LEC1, AGP, Dek1, Superal1, milps, various Ipa genes such as Ipa1, Ipa3, hpt or hggt. For example, see WO 02/42424, WO 98/22604, WO 03/011015, WO02/057439, WO03/011015, U.S. Pat. Nos. 6,423,886, 6,197,561, 6,825,397, and U.S. Application Serial Nos. US2003/0079247, US2003/0204870.

(B) Altered phosphate content, for example, by the (1) Introduction of a phytase-encoding gene would enhance breakdown of phytate, adding more free phosphate to the transformed plant.

(2) Modulating a gene that reduces phytate content. In alfalfa, this, for example, could be accomplished, by cloning and then re-introducing DNA associated with one or more of the alleles, such as the LPA alleles, identified in alfalfa mutants characterized by low levels of phytic acid.

(C) Altered carbohydrates affected, for example, by altering a gene for an enzyme that affects the branching pattern of starch or, a gene altering thioredoxin such as NTR and/or TRX (See U.S. Pat. No. 6,531,648) and/or a gamma zein knock out or mutant such as cs27 or TUSC27 or en27 (See U.S. Pat. No. 6,858,778 and US2005/0160488, US2005/0204418). See e.g., WO 99/10498 (improved digestibility and/or starch extraction through modification of UDP-D-xylose 4-epimerase, Fragile 1 and 2, Ref1, HCHL, C4H) and U.S. Pat. No. 6,232,529 (method of producing high oil seed by modification of starch levels (AGP)). The fatty acid modification genes mentioned herein may also be used to affect starch content and/or composition through the interrelationship of the starch and oil pathways.

(D) Altered antioxidant content or composition, such as alteration of tocopherol or tocotrienols. For example, see U.S. Pat. No. 6,787,683, US2004/0034886 and WO 00/68393 involving the manipulation of antioxidant levels, and WO 03/082899 through alteration of a homogentisate geranyl transferase (hggt).

(E) Altered essential seed amino acids. For example, see U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO99/40209 (alteration of amino acid compositions in seeds), WO99/29882 (methods for altering amino acid content of proteins), U.S. Pat. No. 5,850,016 (alteration of amino acid compositions in seeds), WO98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO98/56935 (plant amino acid biosynthetic enzymes), WO98/45458 (engineered seed protein having higher percentage of essential amino acids), WO98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO96/01905 (increased threonine), WO95/15392 (increased lysine), US2003/0163838, US2003/0150014, US2004/0068767, U.S. Pat. No. 6,803,498, WO01/79516.

4. Genes that Control Male-sterility: There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. In addition to these methods, Albertsen et al., U.S. Pat. No. 5,432,068, describe a system of nuclear male sterility which includes: identifying a gene which is needed for male fertility; silencing this native gene which is needed for male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

(A) Introduction of a deacetylase gene under the control of a tapetum-specific promoter and with the application of the chemical N—Ac-PPT (WO 01/29237).

(B) Introduction of various stamen-specific promoters (WO 92/13956, WO 92/13957).

(C) Introduction of the barnase and the barstar gene.

For additional examples of nuclear male and female sterility systems and genes, see also, U.S. Pat. Nos. 5,859,341; 6,297,426; 5,478,369; 5,824,524; 5,850,014; and 6,265,640.

5. Genes that create a site for site specific DNA integration. This includes the introduction of FRT sites that may be used in the FLP/FRT system and/or Lox sites that may be used in the Cre/Loxp system. For example, see WO 99/25821. Other systems that may be used include the Gin recombinase of phage Mu, the Pin recombinase of *E. coli*, and the R/RS system of the pSR1 plasmid.

6. Genes that affect abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. Nos. 5,892,009; 5,965,705; 5,929,305; 5,891,859; 6,417,428; 6,664,446; 6,706,866; 6,717,034; 6,801,104; WO2000060089; WO2001026459; WO2001035725; WO2001034726; WO2001035727; WO2001036444; WO2001036597; WO2001036598; WO2002015675; WO2002017430; WO2002077185; WO2002079403; WO2003013227; WO2003013228; WO2003014327; WO2004031349; WO2004076638; WO9809521; and WO9938977 describing genes, including CBF genes and transcription factors effective in mitigating the negative effects of freezing, high salinity, and drought on plants, as well as conferring other positive effects on plant phenotype; US2004/0148654 and WO01/36596 where abscisic acid is altered in plants resulting in improved plant phenotype such as increased yield and/or increased tolerance to abiotic stress; WO2000/006341, WO04/090143, U.S.

application Ser. Nos. 10/817,483 and 09/545,334 where cytokinin expression is modified resulting in plants with increased stress tolerance, such as drought tolerance, and/or increased yield. Also see WO0202776, WO2003052063, JP2002281975, U.S. Pat. No. 6,084,153, WO0164898, U.S. Pat. Nos. 6,177,275, and 6,107,547 (enhancement of nitrogen utilization and altered nitrogen responsiveness). For ethylene alteration, see US20040128719, US20030166197 and WO200032761. For plant transcription factors or transcriptional regulators of abiotic stress, see e.g. US20040098764 or US20040078852.

Other genes and transcription factors that affect plant growth and agronomic traits such as yield, flowering, plant growth and/or plant structure, can be introduced or introgressed into plants, see e.g. WO97/49811 (LHY), WO98/56918 (ESD4), WO97/10339 and U.S. Pat. No. 6,573,430 (TFL), U.S. Pat. No. 6,713,663 (FT), WO96/14414 (CON), WO96/38560, WO01/21822 (VRN1), WO00/44918 (VRN2), WO99/49064 (GI), WO00/46358 (FRI), WO97/29123, U.S. Pat. Nos. 6,794,560, 6,307,126 (GAI), WO99/09174 (D8 and Rht), WO2004076638 and WO2004031349 (transcription factors).

Seed Treatments and Cleaning

Methods of harvesting the seeds of variety AFX176086 and using the seeds for planting are provided. Also provided are methods of using the seed of variety AFX176086, or grain harvested from variety AFX176086, as seed for planting. Embodiments include cleaning the seed, treating the seed, and/or conditioning the seed and seed produced by such cleaning, conditioning, treating or any combination thereof. Cleaning the seed is understood in the art to include removal of one or more of foreign debris such as weed seed, chaff, and non-seed plant matter from the seed. Conditioning the seed is understood in the art to include controlling the temperature and rate of dry down of the seed and storing the seed in a controlled temperature environment. Seed treatment is the application of a composition to the seed such as a coating or powder. Methods for producing a treated seed include the step of applying a composition to the seed or seed surface. Seeds are provided which have on the surface a composition. Biological active components such as bacteria can also be used as a seed treatment. Some examples of compositions include active components such as insecticides, fungicides, pesticides, antimicrobials, germination inhibitors, germination promoters, cytokinins, and nutrients. Biological active components, such as bacteria, can also be used as a seed treatment. Carriers such as polymers can be used to increase binding of the active component to the seed.

To protect and to enhance yield production and trait technologies, seed treatment options can provide additional crop plan flexibility and cost effective control against insects, weeds and diseases, thereby further enhancing the invention described herein. Seed material can be treated, typically surface treated, with a composition comprising combinations of chemical or biological herbicides, herbicide safeners, insecticides, fungicides, germination inhibitors and enhancers, nutrients, plant growth regulators and activators, bactericides, nematicides, avicides and/or molluscicides. These compounds are typically formulated together with further carriers, surfactants or application-promoting adjuvants customarily employed in the art of formulation. The coatings may be applied by impregnating propagation material with a liquid formulation or by coating with a combined wet or dry formulation. Examples of the various types of compounds that may be used as seed treatments are provided in The Pesticide Manual: A World Compendium, C.D.S. Tomlin Ed., Published by the British Crop Production Council.

Some seed treatments that may be used on crop seed include, but are not limited to, one or more of abscisic acid, acibenzolar-S-methyl, avermectin, amitrol, azaconazole, azospirillum, azadirachtin, azoxystrobin, *Bacillus* spp. (including one or more of *cereus, firmus, megaterium, pumilis, sphaericus, subtilis* and/or *thuringiensis*), *Bradyrhizobium* spp. (including one or more of *betae, canariense, elkanii, iriomotense, japonicum, liaonigense, pachyrhizi* and/or *yuanmingense*), captan, carboxin, chitosan, clothianidin, copper, cyazypyr, difenoconazole, etidiazole, fipronil, fludioxonil, fluoxastrobin, fluquinconazole, flurazole, fluxofenim, harpin protein, imazalil, imidacloprid, ipconazole, isoflavenoids, lipo-chitooligosaccharide, mancozeb, manganese, maneb, mefenoxam, metalaxyl, metconazole, myclobutanil, PCNB, penflufen, *penicillium*, penthiopyrad, permethrine, picoxystrobin, prothioconazole, pyraclostrobin, rynaxypyr, S-metolachlor, saponin, sedaxane, TCMTB, tebuconazole, thiabendazole, thiamethoxam, thiocarb, thiram, tolclofos-methyl, triadimenol, *trichoderma*, trifloxystrobin, triticonazole and/or zinc. PCNB seed coat refers to EPA registration number 00293500419, containing quintozen and terrazole. TCMTB refers to 2-(thiocyanomethylthio) benzothiazole.

Seed varieties and seeds with specific transgenic traits may be tested to determine which seed treatment options and application rates may complement such varieties and transgenic traits in order to enhance yield. For example, a variety with good yield potential but head smut susceptibility may benefit from the use of a seed treatment that provides protection against head smut, a variety with good yield potential but cyst nematode susceptibility may benefit from the use of a seed treatment that provides protection against cyst nematode, and so on. Likewise, a variety encompassing a transgenic trait conferring insect resistance may benefit from the second mode of action conferred by the seed treatment, a variety encompassing a transgenic trait conferring herbicide resistance may benefit from a seed treatment with a safener that enhances the plants resistance to that herbicide, etc. Further, the good root establishment and early emergence that results from the proper use of a seed treatment may result in more efficient nitrogen use, a better ability to withstand drought and an overall increase in yield potential of a variety or varieties containing a certain trait when combined with a seed treatment.

INDUSTRIAL APPLICABILITY

Another embodiment is a method of harvesting the grain or plant material of the variety AFX176086 and using the grain or plant material in a commodity, such as used for forage. Commodity products may contain at least one cell of alfalfa variety AFX176086 or at least one cell of a modified plant of the variety disclosed herein. Methods of producing a plant product or commodity from the alfalfa variety disclosed herein are also provided. Examples of alfalfa grain or plant material as a commodity plant product include, but are not limited to, hay, haylage, forage, sprouts, meal, cellulose, greenchop, and silage, which can be used as livestock feed. Hay, meal and silage from the alfalfa described herein are provided and their use as livestock feed or bedding, for example for horses, beef cattle, dairy cattle, hogs, sheep, poultry, chickens, turkeys and other farm animals as well as in the pet industry such as for rodents and reptiles. The food and nutritional uses of alfalfa include alfalfa sprouts for human consumption and nutritional supplements.

Processing the seed or grain can include one or more of cleaning to remove foreign material and debris from the seed or grain, conditioning, such as addition of moisture to the grain, steeping the grain, wet milling, dry milling and sifting.

The seed of the alfalfa variety, the plant produced from the seed, a plant produced from crossing of alfalfa variety AFX176086 and various parts of the alfalfa plant and transgenic and locus converted versions of the foregoing, can be utilized for human food, livestock feed, and as a raw material in industry.

All publications, patents, and patent applications mentioned in the specification are incorporated by reference herein for the purpose cited to the same extent as if each was specifically and individually indicated to be incorporated by reference herein.

The foregoing invention has been described in detail by way of illustration and example for purposes of clarity and understanding. As is readily apparent to one skilled in the art, the foregoing are only some of the methods and compositions that illustrate the embodiments of the foregoing invention. It will be apparent to those of ordinary skill in the art that variations, changes, modifications, and alterations may be applied to the compositions and/or methods described herein without departing from the true spirit, concept, and scope of the invention.

As used herein, the terms "comprises," "comprising," "includes," "including," "has," "having," "contains", "containing," "characterized by" or any other variation thereof, are intended to cover a non-exclusive inclusion.

Unless expressly stated to the contrary, "or" is used as an inclusive term. For example, a condition A or B is satisfied by any one of the following: A is true (or present) and B is false (or not present), A is false (or not present) and B is true (or present), and both A and B are true (or present). The indefinite articles "a" and "an" preceding an element or component are nonrestrictive regarding the number of instances (i.e., occurrences) of the element or component. Therefore "a" or "an" should be read to include one or at least one, and the singular word form of the element or component also includes the plural unless the number is obviously meant to be singular.

Deposits

Applicant has made a deposit of at least 625 seeds of alfalfa variety AFX176086 with the Provasoli-Guillard National Center for Marine Algae and Microbiota (NCMA), 60 Bigelow Drive, East Boothbay, Me. 04544, USA, with NCMA Accession Number 202010010, which has been accepted under the Budapest Treaty. The seeds deposited with the NCMA on Oct. 1, 2020 were obtained from the seed of the variety maintained by Agrigenetics, Inc., 9330 Zionsville Road, Indianapolis, Ind. 46268 since prior to the filing date of this application. Access to this seed will be available during the pendency of the application to the Commissioner of Patents and Trademarks and persons determined by the Commissioner to be entitled thereto upon request. Upon allowance of any claims in the application, the Applicant will make the deposit available to the public pursuant to 37 C.F.R. § 1.808. This deposit of the Alfalfa Variety AFX176086 will be maintained in the NCMA depository, which is a public depository, for a period of 30 years, or 5 years after the most recent request, or for the enforceable life of the patent, whichever is longer, and will be replaced if it becomes nonviable during that period. Additionally, Applicant has or will satisfy all of the requirements of 37 C.F.R. §§ 1.801-1.809, including providing an indication of the viability of the sample upon deposit. Applicant has no authority to waive any restrictions imposed by law on the transfer of biological material or its transportation in commerce. Applicant does not waive any infringement of rights granted under this patent or under the Plant Variety Protection Act (7 USC 2321 et seq.).

Example 1: Breeding History

Alfalfa variety AFX176086 is a synthetic variety developed with parent plants selected sequentially for resistance to *Phytophthora* root rot, and Anthracnose. Parent plants were selected from various proprietary populations that were developed by phenotypic recurrent selection for winter hardiness, high forage dry matter yield, high forage quality, and for resistance to one or more of the following pests: Bacterial wilt, *Fusarium* Wilt, *Verticillium* wilt, *Phytophthora* root rot, *Aphanomyces* root rot (race 1 and race 2), Anthracnose (race 1), and *Leptosphaerulina* leaf spot. Parentage of variety AFX176086 traces to proprietary non-public breeding populations.

Example 2: Variety Description

Alfalfa variety AFX176086 is a moderately dormant variety with fall dormancy similar to FD class 6 check varieties. Flower color observed in the Syn.2 generation is approximately 90% purple, 9% variegated and a trace of cream, white, and yellow. Alfalfa variety AFX176086 has high resistance to Anthracnose (race 1), *Aphanomyces* root rot (race 1), Bacterial wilt, *Fusarium* wilt, *Phytophthora* root rot, and *Verticillium* wilt. It has resistance to Blue aphid, Pea aphid, Spotted alfalfa aphid, Cowpea aphid, and Stem nematode.

The characteristics of alfalfa variety AFX176086 are described in the following tables.

TABLE 1

Yield data for AFX176086 in DM in T/A compared to other varieties at multiple locations.

| Test Location | Syn Gen | No. Cuts | AFX176086 | 54Q14 | L-504HD | LegenDairy XHD | LSD .05 | CV % |
| --- | --- | --- | --- | --- | --- | --- | --- | --- |
| Mankato, MN | 1 | 4 | 6.53 | 6.62 | 6.95 | 6.49 | 0.68 | 6.12 |
| | | 3 | 5.21 | 5.22 | 5.44 | 5.59 | 0.39 | 4.14 |
| Arlington, WI | 1 | 4 | 3.82 | 5.19 | 4.59 | 4.62 | 1.10 | 12.84 |
| | | 4 | 3.05 | 4.00 | 3.40 | 3.52 | 0.76 | 11.34 |

TABLE 1-continued

Yield data for AFX176086 in DM in T/A compared to other varieties at multiple locations.

| Test Location | Syn Gen | No. Cuts | AFX176086 | 54Q14 | L-504HD | LegenDairy XHD | LSD .05 | CV % |
|---|---|---|---|---|---|---|---|---|
| West Salem, WI | 2 | 5 | 5.16 | 4.74 | 5.03 | 5.02 | 0.53 | 5.81 |
|  |  | 4 | 5.37 | 4.41 | 4.81 | 5.19 | 0.65 | 6.76 |

TABLE 2

Mean Annual Yield in Tons DM/Acre.

| Variety names | # of Years Harvested | Total # of Harvests | AFX176086 | 54Q14 | L-504HD | LegenDairy XHD |
|---|---|---|---|---|---|---|
| AFX176086 | 6 | 24 | 4.86 |  |  |  |
| Check 1 (54Q14) | 6 | 24 | 4.86 | 5.03 |  |  |
| Check 2 (L-504HD) | 6 | 24 | 4.86 |  | 5.04 |  |
| Check 3 (LegenDairy XHD) | 6 | 24 | 4.86 |  |  | 5.07 |

TABLE 3

Persistence data for AFX176086 compared to other varieties (Percent of stand).

| | | | % Stand | | | | |
|---|---|---|---|---|---|---|---|
| | | | | Check Varieties | | | |
| Syn Gen | No. of Years Harvested | No. of Harvests | AFX176086 Initial/Final | L-504HD Initial/Final | LegenDairy XHD Initial/Final | LSD .05 | CV % |
| 1 | 3 | 12 | 99/82 | 99/73 | 99/70 | 5.61 | 4.10 |

TABLE 4

Fall dormancy as determined from spaced plantings

| | FDC[1] | Average Height Fall Regrowth (cm) | Syn Gen | LSD .05 | CV % |
|---|---|---|---|---|---|
| AFX176086 | 6 | 29.83 | 1 | 2.32 | 6.50 |

Check Varieties - Height of fall regrowth (cm)

| Legend | 22.08 |
|---|---|
| Archer | 27.08 |
| ABI 700 | 31.25 |
| Doña Ana | 33.25 |

[1]Fall dormancy class used by the NAFA. (6 = Moderately-Dormant to Non-Dormant)

TABLE 5

Multifoliate Leaf Expression for AFX176086

| Variety | | Multifoliolate Leaf Expression Score | Syn Gen | MFI | % MF |
|---|---|---|---|---|---|
| AFX176086* | | 1.13 | 1 | 1.09 | 13 |
| | Range | | | | |
| Vernal | 1.00 | 1.00-1.05 | 1.07 | 1.02 | 7 |
| Legend | 1.86 | 1.40-2.40 | 1.53 | 1.47 | 40 |
| MultiKing I | 2.55 | 2.00-3.00 | 2.47 | 2.37 | 69 |
| Proof | 3.35 | 2.80-3.80 | 3.49 | 3.35 | 93 |
| Test Mean: | | | 2.10 | 2.02 | 59 |
| L.S.D. (.05%) | | | 0.58 | 0.56 | 27 |
| C. V. (%) | | | 16.96 | 16.96 | 28 |

*AFX176086 is most similar to Vernal in multifoliate leaf expression

TABLE 6

Anthracnose (Race 1) Disease Scores for AFX176086 - greenhouse test.

| Variety | Resistance Class | Syn Gen | Unadjusted % R | Adjusted % R | Score |
|---|---|---|---|---|---|
| AFX176086 | HR | 1 | 61 | 67 | |
| Arc | HR | | 60 | 65 | |
| Saranac AR | R | | 40 | 44 | |
| Saranac | S | | 4 | 4 | |
| Test Mean: | | | 48 | 53 | |
| L.S.D. (.05%) | | | 10 | 11 | |
| C.V. (%) | | | 14 | 14 | |

TABLE 7

Bacterial Wilt Disease Scores for AFX176086 - greenhouse test

| Variety | Resistance Class | Syn Gen | Unadjusted % R | Adjusted % R | Score |
|---|---|---|---|---|---|
| AFX176086 | HR | 1 | 53 | 55 | 2.56 |
| Vernal | R | | 41 | 42 | 2.80 |
| Narragansett | S | | 0 | 0 | 3.49 |
| Sonora | S | | 0 | 0 | 3.55 |
| Test Mean: | | | 46 | 47 | 2.66 |
| L.S.D. (.05%) | | | 8 | 8 | 0.18 |
| C.V. (%) | | | 11 | 11 | 4.83 |

TABLE 8

Fusarium Wilt Disease Scores for AFX176086 - field test.

| Variety | Resistance Class | Syn Gen | Unadjusted % R | Adjusted % R | Score |
|---|---|---|---|---|---|
| AFX176086 | HR | 1 | 55 | 57 | 2.49 |
| Agate | HR | | 52 | 54 | 2.45 |
| Moapa 69 | HR | | 65 | 68 | 2.34 |
| Narragansett | MR | | | | |
| MNGN-1 | S | | 0 | 0 | 3.83 |
| Test Mean: | | | 60 | 62 | 2.38 |
| L.S.D. (.05%) | | | 9 | 10 | 0.20 |
| C.V. (%) | | | 11 | 11 | 6.10 |

TABLE 9

Verticillium Wilt Disease Scores for AFX176086 - greenhouse test

| Variety | Resistance Class | Syn Gen | Unadjusted % R | Adjusted % R | Score |
|---|---|---|---|---|---|
| AFX176086 | HR | 1 | 51 | 55 | 2.71 |
| Vertus | R | | 40 | 44 | 2.84 |
| Oneida VR | HR | | 55 | 60 | 2.60 |
| Saranac | S | | 1 | 1 | 3.69 |
| Test Mean: | | | 45 | 49 | 2.79 |
| L.S.D. (.05%) | | | 7 | 8 | 0.24 |
| C.V. (%) | | | 12 | 12 | 6.07 |

TABLE 10

Phytophthora Root Rot Disease Scores for AFX176086 - seedling and greenhouse test.

| Variety | Resistance Class | Syn Gen | Unadjusted % R | Adjusted % R | Score |
|---|---|---|---|---|---|
| AFX176086 | HR | 1 | 59 | 64 | |
| WAPH-1 (seedling) | HR | | 53 | 55 | |
| MNP-D1 (seedling) | R | | | | |
| Agate | R | | | | |
| Saranac | S | | 1 | 1 | |
| Test Mean: | | | 39 | 41 | |
| L.S.D. (.05%) | | | 7 | 8 | |
| C.V. (%) | | | 14 | 14 | |

TABLE 11

Aphanomyces Root Rot Disease Scores for AFX176086 - greenhouse test - Race 1.

| Variety | Resistance Class | Syn Gen | Unadjusted % R | Adjusted % R | Score |
|---|---|---|---|---|---|
| AFX176086 | HR | 1 | 55 | 54 | 2.68 |
| WAPH-1 (Race 1) | R | | 51 | 50 | 2.58 |
| WAPH-1 (Race 2) | S | | | | |
| WAPH-5 (Race 2) | R | | | | |
| Saranac (Races 1 & 2) | S | | 0 | 0 | 3.72 |
| Test Mean: | | | 59 | 59 | 2.44 |
| L.S.D. (.05%) | | | 7 | 7 | 0.23 |
| C.V. (%) | | | 8 | 8 | 6.70 |

TABLE 12

Pea Aphid Insect Scores for Scores for AFX176086 - greenhouse test.

| Variety | Resistance Class | Syn Gen | Unadjusted % R | Adjusted % R | Score |
|---|---|---|---|---|---|
| AFX176086 | R | 1 | 28 | 38 | 4.13 |
| CUF-101 | HR | | 41 | 55 | 3.67 |
| PA-1 | HR | | | | |
| Kanza | R | | | | |
| Baker | R | | | | |
| Caliverde | S | | | | |
| Moapa 69 | S | | | | |
| Vernal | S | | | | |
| Ranger | S | | 1 | 1 | 4.75 |
| Test Mean: | | | 26 | 36 | 4.08 |
| L.S.D. (.05%) | | | 10 | 13 | 0.32 |
| C.V. (%) | | | 27 | 27 | 5.49 |

TABLE 13

Spotted Alfalfa Aphid Insect Scores for AFX176086 - greenhouse test.

| Variety | Resistance Class | Syn Gen | Unadjusted % R | Adjusted % R | Score |
|---|---|---|---|---|---|
| AFX176086 | R | 1 | 33 | 42 | 3.08 |
| CUF-101 | HR | | 47 | 60 | 2.68 |
| Baker | R | | | | |
| Mesa Sirsa | R | | | | |
| Kanza | R | | | | |
| Caliverde | S | | | | |
| Arc | S | | | | |
| OK08 | S | | | | |

TABLE 13-continued

Spotted Alfalfa Aphid Insect Scores for AFX176086 - greenhouse test.

| Variety | Resistance Class | Syn Gen | Unadjusted % R | Adjusted % R | Score |
|---|---|---|---|---|---|
| Ranger | S | | 1 | 1 | 4.14 |
| Test Mean: | | | 32 | 42 | 3.09 |
| L.S.D. (.05%) | | | 11 | 15 | 0.32 |
| C.V. (%) | | | 25 | 25 | 7.24 |

TABLE 14

Blue Alfalfa Aphid Insect

| Variety | Resistance Class | Syn Gen | Unadjusted % R | Adjusted % R | Score |
|---|---|---|---|---|---|
| AFX176086 | R | 1 | 34 | 46 | 3.82 |
| CUF-101 | HR | | 41 | 55 | 3.54 |
| OK51 | R | | | | |
| PA-1 | LR | | | | |
| Arc | S | | | | |
| Caliverde | S | | 0 | 0 | 4.33 |
| Test Mean: | | | 31 | 42 | 3.72 |
| L.S.D. (.05%) | | | 11 | 15 | 0.24 |
| C.V. (%) | | | 25 | 25 | 4.50 |

TABLE 15

Stem Nematode Scores for AFX176086 - greenhouse test.

| Variety | Resistance Class | Syn Gen | Unadjusted % R | Adjusted % R | Score |
|---|---|---|---|---|---|
| AFX176086 | R | 1 | 39 | 45 | |
| Vernema | HR | | 52 | 60 | |
| Lahontan | R | | | | |
| Lew | R | | | | |
| Ranger | S | | 10 | 12 | |
| Moapa 69 | S | | | | |
| Test Mean: | | | 39 | 45 | |
| L.S.D. (.05%) | | | 17 | 20 | |
| C.V. (%) | | | 31 | 31 | |

TABLE 16

Cowpea Aphid Scores for AFX176086 - lab greenhouse test

| Variety | Resistance Class | Syn Gen | Unadjusted % R | Adjusted % R | Score |
|---|---|---|---|---|---|
| AFX176086 | R | 1 | 36 | 42 | 2.81 |
| CW 30044 | HR | | 48 | 55 | 2.46 |
| CUF 101 | MR | | | | |
| Ranger | S | | 1 | 2 | 0.05 |
| Test Mean: | | | 40 | 47 | 2.68 |
| L.S.D. (.05%) | | | 8 | 10 | 0.25 |
| C.V. (%) | | | 15 | 15 | 6.59 |

All disease tests conducted for National Alfalfa and Miscellaneous Legume Variety Review Board for AOSCA certification and were conducted by standard procedures and scoring systems as described in the NAAIC Standard Tests to Characterize Alfalfa Cultivars, maintained online on the NAAIC website.

We claim:

1. A seed of alfalfa variety AFX176086, representative seed having been deposited under NCMA Accession Number 202010010.

2. An alfalfa plant, or a plant part thereof, produced by growing the seed of claim 1, wherein the plant part comprises at least one cell of alfalfa variety AFX176086.

3. A pollen grain or ovule of the plant of claim 2.

4. A tissue culture of regenerable cells or regenerable protoplasts from the plant of claim 2, wherein the tissue culture comprises somatic cells.

5. The tissue culture according to claim 4, wherein a cell or protoplast of the tissue culture is derived from a tissue or cell selected from the group consisting of leaves, roots, root tips, root hairs, anthers, pistils, stamens, pollen, ovules, flowers, seeds, stems, buds, cotyledons, hypocotyls, cells and protoplasts.

6. An alfalfa plant regenerated from the tissue culture of claim 4, wherein the regenerated plant has all of the morphological and physiological characteristics of alfalfa variety AFX176086, representative seed of said alfalfa variety having been deposited under NCMA Accession Number 202010010.

7. A method for producing a first generation progeny alfalfa seed comprising crossing the plant of claim 2 with a second alfalfa plant or self-pollinating the plant of claim 2 and harvesting the resultant alfalfa seed.

8. A method for producing an alfalfa plant, the method comprising introducing a locus conversion or a transgene into the plant or plant part of claim 2.

9. An alfalfa plant produced by the method of claim 8; wherein the alfalfa plant produced comprises the locus conversion or transgene and otherwise comprises all of the physiological and morphological characteristics of a plant of the alfalfa variety AFX176086.

10. A seed that produces the plant of claim 9, wherein the seed comprises the locus conversion or transgene and produces a plant that otherwise comprises all of the physiological and morphological characteristics of a seed of the alfalfa variety AFX176086.

11. The plant of claim 9, wherein the transgene or locus conversion confers a trait selected from the group consisting of herbicide resistance, insect resistance, disease resistance, improved digestibility, improved energy content, male sterility, and improved winterhardiness.

12. A method for introducing a transgene or a single locus conversion into a population of alfalfa plants, the method comprising the steps of: (a) modifying the plant or plant part of claim 2 by introducing a transgene or a single locus conversion; and (b) crossing the modified alfalfa plant or plant part of step (a) with a population of alfalfa plants to produce a population of progeny plants, wherein at least one progeny plant comprises the transgene or single locus conversion.

13. A method for producing a synthetic alfalfa variety, the method comprising crossing a plant grown from the seed of claim 1 with a plant grown from seed of one or more different alfalfa plants.

14. A method for producing alfalfa seed, the method comprising growing the plant of claim 2 and allowing the plant to cross pollinate with one or more different alfalfa plants.

15. A method of producing a commodity plant product, the method comprising producing the commodity plant product from the plant of claim 2, wherein the commodity plant product is selected from the group consisting of forage, hay, meal, greenchop, and silage.

16. A commodity plant product produced by the method of claim 15, wherein the commodity plant product comprises at least one cell of said alfalfa variety AFX176086.

17. The seed of claim 1, further comprising a seed treatment on the surface of the seed.

18. A method comprising cleaning the seed of claim 1.

19. The method of claim 12, further comprising the step of: (c) applying a selection technique to the population produced in (b) to select the progeny plants that comprise the transgene or single locus conversion.

20. A method for producing nucleic acids, the method comprising isolating nucleic acids from the seed of claim 1.

* * * * *